United States Patent
Norrman et al.

(10) Patent No.: US 10,040,073 B2
(45) Date of Patent: Aug. 7, 2018

(54) EXTRACTION SEPARATION USING MAGNETIC BEADS

(71) Applicant: GE HEALTHCARE BIO-SCIENCES AB, Uppsala (SE)

(72) Inventors: Nils Norrman, Uppsala (SE); Pierre Le Greves, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 364 days.

(21) Appl. No.: 14/764,919

(22) PCT Filed: Jan. 29, 2014

(86) PCT No.: PCT/EP2014/051728
§ 371 (c)(1),
(2) Date: Jul. 30, 2015

(87) PCT Pub. No.: WO2014/118237
PCT Pub. Date: Aug. 7, 2014

(65) Prior Publication Data
US 2015/0360232 A1  Dec. 17, 2015

(30) Foreign Application Priority Data

Jan. 30, 2013 (GB) .................................. 1301631.6

(51) Int. Cl.
*B03C 1/00* (2006.01)
*B03C 1/01* (2006.01)
(Continued)

(52) U.S. Cl.
CPC ............ *B03C 1/02* (2013.01); *B01D 11/0419* (2013.01); *B01D 11/0423* (2013.01);
(Continued)

(58) Field of Classification Search
CPC .... B03C 1/00; B03C 1/01; B03C 1/02; B01D 11/0423; B01D 11/0419; B01D 15/3885;
(Continued)

(56) References Cited

U.S. PATENT DOCUMENTS 3,806,449 A  4/1974 Kaiser
3,923,651 A  12/1975 Weiss et al.
(Continued)

FOREIGN PATENT DOCUMENTS

CN  101231899 A  7/2008
EP    0179039 A2  10/1985
(Continued)

OTHER PUBLICATIONS

International Search Report dated May 8, 2014 which was issued in connection with PCT Patent Application No. PCT/EP2014/051728 which was filed on Jan. 29, 2014.
(Continued)

*Primary Examiner* — David A Reifsnyder
(74) *Attorney, Agent, or Firm* — Wood IP LLC

(57) ABSTRACT

A method for purifying a substance in a solution in a simple streamlined process using a magnetic porous particle. For easy small scale purification of a substance, the magnetic porous particle is coated with either a hydrophilic or hydrophobic liquid and transferred into a second liquid containing the substance under conditions which allow said substance to partition into the first liquid within said magnetic porous particle. Finally the magnetic porous particle is removed from said second liquid, wherein the first and second liquid are substantially immiscible and the partition coefficient P of the substance between the first and second liquid is greater than 1.

26 Claims, 1 Drawing Sheet

(51) Int. Cl.
  *B03C 1/02*  (2006.01)
  *B01D 11/04*  (2006.01)
  *B01D 15/38*  (2006.01)
  *B01J 20/24*  (2006.01)
  *B01J 20/26*  (2006.01)
  *B01J 20/28*  (2006.01)
  *B01J 20/32*  (2006.01)
  *C02F 1/48*  (2006.01)
  *C07K 1/14*  (2006.01)
  *H01F 1/44*  (2006.01)
  *C02F 101/30*  (2006.01)

(52) U.S. Cl.
  CPC .......... *B01D 15/3885* (2013.01); *B01J 20/24* (2013.01); *B01J 20/261* (2013.01); *B01J 20/28009* (2013.01); *B01J 20/3204* (2013.01); *B01J 20/327* (2013.01); *B01J 20/3227* (2013.01); *B01J 20/3272* (2013.01); *B01J 20/3289* (2013.01); *B01J 20/3293* (2013.01); *B03C 1/00* (2013.01); *B03C 1/01* (2013.01); *C02F 1/48* (2013.01); *C07K 1/14* (2013.01); *H01F 1/445* (2013.01); *B01J 2220/64* (2013.01); *C02F 2101/308* (2013.01)

(58) Field of Classification Search
  CPC .... B01J 20/24; B01J 20/261; B01J 20/28009; B01J 20/3272; B01J 20/3293; B01J 20/3289; B01J 20/3204; B01J 20/327; B01J 20/3227; B01J 2220/64; C02F 1/48; C02F 2101/308; C07K 1/14; H01F 1/445
  See application file for complete search history.

(56) References Cited

U.S. PATENT DOCUMENTS

| | | |
|---|---|---|
| 4,108,767 A | 8/1978 | Cooper |
| 4,612,247 A | 9/1986 | Walsh et al. |
| 5,043,070 A | 8/1991 | Hwang |
| 5,834,121 A | 11/1998 | Sucholeiki et al. |
| 6,204,033 B1 | 3/2001 | Muller-Schulte |
| 6,274,387 B1 | 8/2001 | Yamauchi et al. |
| 7,897,257 B2 | 3/2011 | Alterman et al. |
| 2010/0116747 A1 | 5/2010 | Franzreb et al. |

FOREIGN PATENT DOCUMENTS

| | | |
|---|---|---|
| EP | 0221046 A2 | 10/1986 |
| EP | 0937497 A2 | 8/1999 |
| WO | 2007050017 A1 | 5/2007 |

OTHER PUBLICATIONS

GB Search Report dated Jul. 24, 2013 which was issued in connection with GB Patent Application No. 1301631.6 which was filed on Jan. 30, 2013.

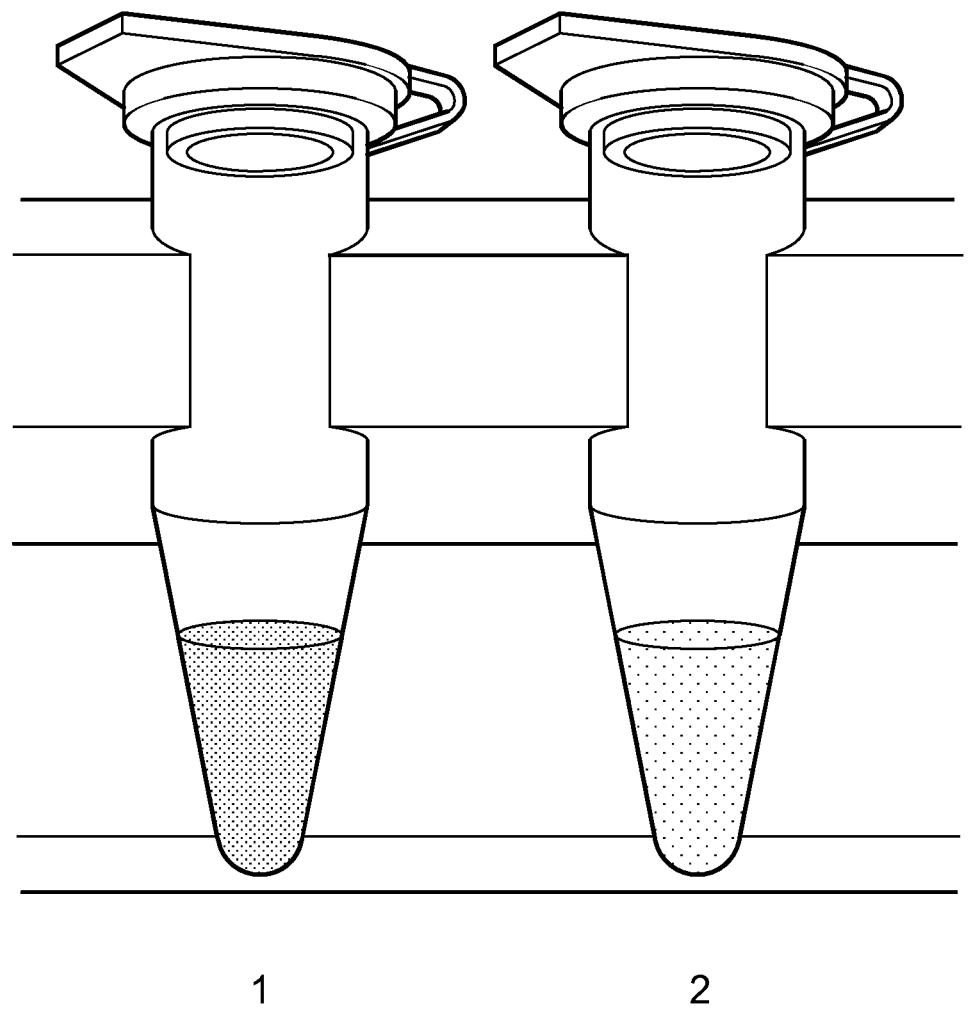
1    2

EXTRACTION SEPARATION USING MAGNETIC BEADS

CROSS-REFERENCE TO RELATED APPLICATIONS

This is a national stage application under 35 U.S.C. § 371(c) of prior filed, co-pending PCT application serial number PCT/EP2014/051728, filed on Jan. 29, 2014, which claims priority to Great Britain Patent Application Serial No. 1301631.6, filed Jan. 30, 2013 and titled SEPARATION OF SUBSTANCES USING MAGNETIC BEADS. The above-listed applications are herein incorporated by reference.

FIELD OF INVENTION

Embodiments of the present invention relate to the field of chemical purification. Embodiments of the present invention provide a method which can be used to purify a substance in a solution in a simple streamlined process using a magnetic porous particle. Embodiments of the present invention has particular application in the small scale purification of substances such as drugs, proteins, lipids, carbohydrates and nucleic acids from a solution.

BACKGROUND

There are several methods available to separate and purify molecules in a solution. Several different complementary chromatographic techniques are often used serially, e.g. gel filtration, ion exchange chromatography, hydrophobic interaction chromatography and bioaffinity chromatography. The use of several chromatographic steps is cumbersome and can be costly particularly when working at a micro scale.

Magnetic beads are used for diverse purposes such as isolating nucleic acids and proteins as well as viruses and whole cells. The most commonly used magnetic bead is that which is used in combination with attached ligands which have an affinity for different substances.

EP0221046 (Monsanto Company) describes pore surfaces in membranes/matrices that can be coated with polymers of such molecular weight that clogging of the pores is prevented.

U.S. Pat. No. 5,834,121 (Sucholeiki et al.) describes a composite magnetic bead and a method of making a composite magnetic bead. The polymer coated metal oxide particles are encapsulated in a rigid and solvent stable polymer of vinyl monomers in order to retain the metal oxide particles during harsh conditions. The primary beads are enclosed in a micro porous polymer bead which is capable of swelling in organic solvents and allowing for further functionalization in order to be useful for organic synthesis. The procedure aims to produce a hydrophobic bead.

U.S. Pat. No. 6,204,033 (Muller-Schulte) describes the preparation of polyvinyl alcohol-based magnetic beads for binding biomolecules. The spherically shaped polyvinyl alcohol polymer particles are prepared encapsulating a magnetic colloid. The beads are particularly suited to use in cell separation/sorting, cleaning biosubstances in suspension and diagnostic assays. The polymer particles contain reactive hydroxyl groups and can be provided with spacer molecules to which biomolecules can bind.

U.S. Pat. No. 6,274,387 (Yamauchi et al.) describes a magnetic carrier, preparation thereof, and a method of extraction of nucleic acid. The magnetic carrier comprises particulate silica containing a magnetic material, having a polyacrylamide on the surface.

EP 0179039 (Exploaterings AB T.B.F) describes a particle consisting of a solid core with a surface containing immobilised metal ions and surface coated with a polymer used for the separation of biomolecules. This reference is based on the ability of metals and metal ions to combine with a polymer that has been substituted with a metal chelate builder, in addition they contain an excess of hydroxyl groups which can be used for coupling biologically active components.

U.S. Pat. No. 7,897,257 (Alterman et al.) describes a bead with an inner core of magnetic particles, which are coated in an inert synthetic polymer and then enclosed in a hydrophilic porous polymer, preferably agarose. The applications of the magnetic bead include use for cell cultivation and chromatography. Use in chromatography would require that the agarose layer is provided with ligands that have an affinity for a specific biomolecule. Superdex®, marketed by GE Healthcare Lifesciences, is a porous particles of cross linked agarose coated with dextran on the exterior and the interior.

While several magnetic beads have been previously described there is a need for a small scale (a volume less than 10 L), simple and cost effective method of separating chemicals.

SUMMARY OF THE INVENTION

The present invention provides a method which can be used to purify a substance in a solution in a simple streamlined process using a porous particle.

According to a first aspect of the present invention, there is provided a method of extracting a substance from a liquid comprising the steps of:

i) contacting a porous particle comprising a superparamagnetic or ferromagnetic material with a first liquid, ii) transferring said porous particle to a second liquid containing a substance under conditions to allow said substance to partition into said first liquid within said porous particle, iii) separating the porous particle from said second liquid, wherein the first and second liquid are substantially immiscible and the partition coefficient P of the substance between the first and second liquid is greater than 1.

The advantage of purifying a substance using a porous particle is to reduce the number of purification steps required, thus saving operator time and facilitating operator usage.

In one aspect, the porous particle comprises a plurality of pores each having a pore surface.

In another aspect, the pore surface has a higher affinity for the first liquid than for the second liquid.

In a further aspect, the superparamagnetic material is coated with an inert synthetic polymer.

In another aspect, the superparamagnetic material is ferric oxide.

In a further aspect, the porous particle comprises a natural or a synthetic hydrophilic polymer.

In one aspect, said hydrophilic polymer is selected from the group consisting of agarose, dextran, cellulose, polyvinyl alcohol, polyacrylamide, hydrophilized polymers and silica glass.

In another aspect, the porous particle comprises a natural or a synthetic hydrophobic polymer.

In a further aspect, the hydrophobic polymer is selected from the group consisting of polyvinyl benzene, polymethacrylate, polystyrene, polypropene and polythene.

In one aspect, the porous particle comprises a surface coated or coupled or functionalized with a hydrophobic agent.

In another aspect, said hydrophobic agent is selected from the group consisting of a hydrocarbon group, an aliphatic group and an aromatic group.

In a further aspect, the porous particle comprises a surface coated or coupled or functionalized with a hydrophilic agent.

In another aspect, said hydrophilic agent is selected from the group consisting of a polysaccharide, agarose, dextran, cellulose, sugars, sorbitol and manitol.

In a further aspect, the first liquid is hydrophilic and the second liquid is hydrophobic.

In a further aspect, the first liquid is hydrophobic and the second liquid is hydrophilic.

In a further aspect, the mean particle diameter of the porous particle is in the range of 5 µm to 1000 µm such as 10 µm to 400 µm or 10 µm to 50 µm depending on the use of the magnetic beads.

In another aspect the mean particle diameter of the porous particle is in the range of 30 µm to 200 µm.

In an embodiment of the invention, the magnetic metal particles are made of $FE_3O_4$, the inner coating is made of poly(divinylbenzene), the outer coating is made of agarose. The pore size of the bead composite is 1 nm-1 µm, preferably 50-500 nm.

In one aspect, the volume of the second liquid is selected from the group in the range of 1 µl to 10 µl, 10 µl to 100 µl, 100 µl to 1 ml, 1 ml to 1 L and 1 L to 10 L.

In another aspect, the method of separating the porous particle from said second liquid in step iii) is by magnetic separation.

In a further aspect, the method of separating the porous particle from said second liquid in step iii) is by centrifugation.

In a further aspect, the method of separating the porous particle from said second liquid in step iii) is by filtration.

In another aspect, the method is for use in separating, purifying or concentrating a substance which is present alone or in a mixture in a liquid.

In a further aspect, the substance is a synthetic compound.

In one aspect, the substance is an organic molecule and/or biological molecule.

In another aspect, the substance is selected from the group consisting of lipid, nucleic acid, protein, glycoprotein, glycopeptide, phosphoprotein, phosphopeptide and carbohydrate.

In a further, the substance is selected from the group consisting of agrochemical, pesticide, plasticizer, drug, cosmetic, dye and environmental pollutant.

In one aspect the method of the invention additionally comprises the steps of immersing the porous particle in a third liquid to partition the substance therein, and removing the porous particle from the third liquid.

In a further aspect the invention additionally comprises the step of concentrating the substance in the third liquid.

In another aspect, the third liquid is a hydrophilic liquid.

In another aspect, the third liquid is a hydrophobic liquid.

In one aspect, the method of removing the porous particle from said third liquid in step v) is magnetic separation.

In another aspect, the method of removing the porous particle from said third liquid in step v) is centrifugation.

In a further aspect, the method of removing the porous particle from said third liquid in step v) is filtration.

BRIEF DESCRIPTION OF THE DRAWINGS

FIG. 1 presents the results of the Magnetic Sepharose N6 beads after the addition of HCl and after the subsequent addition of NaOH.

DETAILED DESCRIPTION

Definitions

To more clearly and concisely described and point out the subject matter of the claimed invention, the following definitions are provided for specific terms, which are used in the following description and the appended claims. Throughout the specification, exemplification of specific terms should be considered as non-limiting examples.

The term "immiscible" as used herein will mean a liquid substance that in some proportion doesn't form a homogenous solution.

As used herein, the term "partition coefficient" will mean the equilibrium concentration of a substance in liquid 1 divided by the equilibrium concentration of a substance in liquid 2.

Chemicals and Materials Used

A list of the chemicals and their sources is given below:
2,6-dichloroindophenol (Sigma, no D1878-5G) 0.5 mg/ml in 20 mM NaOH
Chloroform (Sigma, no 288306-100 ml)
0.2M HCL (Merck 1.00317.1000)
0.5M NaOH (Merck, 1.006460.1000)
1.5 ml Eppendorf tube (Axygen, no 311-08-081)
MagRack 6 (GE Healthcare UK Ltd. Product code 28-9489-64)
SpectraMax Spectrophotometer (Molecular Devices)

Experimental Description and Results

Production of Magnetic Sepharose Beads

The Magnetic Sepharose N6 beads were produced using the protocol described in U.S. Pat. No. 7,897,257 (Alterman et al.). The magnetic metal particles were treated with an amphiphilic agent, after which a polymerizable monomer and a radical initiator were added. The temperature was increased to cause the polymerization of the monomer. The polymer-coated magnetic particles are then emulsified into agarose.

The Magnetic Sepharose C8 beads were produced by further reacting the Magnetic Sepharose N6 beads with allyl glycidyl ether and then substituted with Octyl-thiol.

Hydrophilic Magnetic Sepharose N6 Beads
Experimental Method

The dye, 2,6-dichloroindophenol, used in the experiment is blue and water soluble at a neutral to basic pH. At acidic pH it is protonated, red in colour and organic soluble.

100 µl of magnetic slurry yields 22 µl of drained beads, 100 µl of the slurry was added to microtubes and the supernatant (20% EtOH) was removed. The beads were washed twice with 500 µl $dH_2O$.

The Magnetic Sepharose N6 Beads (Mag-N6) were equilibrated twice with 1 ml of dH2O in order to saturate the beads with the solution. MagRack 6 was used to attract the magnetic beads to the base of the microtube and the water was removed. 1 ml of chloroform was added to Mag-N6 (saturated with water) and 50 µl of 2,6-dichloroindophenol (0.5 mg/ml) was added to the tube. The mixture was acidified by the addition of 20 µl 0.2 M HCl. pH was thereafter adjusted to basic by the addition of 8 µl 0.5M NaOH.

Hydrophobic Magnetic Sepharose C8 Beads
Experimental Method

The dye, 2,6-dichloroindophenol, used in the experiment is blue and water soluble at a neutral to basic pH. At acidic pH it is protonated, red in colour and organic soluble.

100 µl of magnetic slurry yields 22 µl of drained beads, 100 µl of the slurry was added to microtubes and the supernatant (20% EtOH) was removed. The beads were washed twice with 500 µl dH$_2$O.

The Magnetic Sepharose C8 Beads (Mag-C8) was equilibrated twice with 1 ml of chloroform in order to saturate the beads with the solution. MagRack 6 was used to attract the magnetic beads to the base of the microtube and the chloroform was removed. 1 ml of water was added to Mag-C8 (saturated with chloroform) and 50 µl of 2,6-dichloroindophenol (0.5 mg/ml) was added to the tube. The mixture was acidified by the addition of 20 µl 0.2 M HCl. Using the MagRack 6 the acidic solution was replaced with 20 mM NaOH.

Results

Magnetic Sepharose N6 Beads Results

After the addition of 2,6-dichloroindophenol to the chloroform solution, the blue dye immediately localized into the hydrophilic water saturated Mag-N6 beads.

The addition of 20 µl of 0.2 M HCl caused a protonation of the dye and the delocalisation of the dye from the beads to the surrounding chloroform phase indicated by the colour red. This process was reversed by the addition of 8 µl of 0.5M NaOH to the chloroform, deprotonating 2,6-dichloroindophenol. The dye turned blue and water soluble and returned into the beads leaving a colourless chloroform solution. The results are presented graphically in FIG. 1.

FIG. 1 shows the results after the addition of HCl (lane 1) and after the subsequent addition of NaOH (lane 2).

Magnetic Sepharose C8 Hydrophobic Beads
Results 2,6-dichloroindophenol indicator was added to the tube containing the chloroform saturated Mag-C8 beads, the indicator was blue as it remained in the water. 20 µl of 0.2M HCL was added to the Mag-C8 beads and the water phase containing the indicator turned red indicating that the dye was protonated.

The beads were subsequently vortexed and the water turned slightly pink because the indicator was localised into the chloroform saturated Mag-C8 bead. The water phase was removed and replaced with 20 mM NaOH and water. The beads were vortexed and the indicator in its deprotonated blue form was delocalized back into the water phase. The absorbance was measured at 590 nm, which is the peak absorbance for the deprotonated blue form of the 2,6-dichloroindophenol indicator. It was calculated that 84% of the dye had been extracted into the chloroform saturated Mag-C8 beads.

While illustrative embodiments of the present invention are described, one skilled in the art will appreciate that the present invention can be practised by other than the described embodiments, which are presented for the purposes of illustration only and not by way of limitation. The present invention is limited only by the claims that follow.

The invention claimed is:

1. A method of extracting a substance from a liquid, the method comprising;
    contacting a porous particle comprising a superparamagnetic or ferromagnetic material with a first liquid;
    transferring said porous particle to a second liquid containing a substance under conditions to allow said substance to partition into said first liquid within said porous particle; and
    separating the porous particle from said second liquid,
    wherein the first and second liquid are substantially immiscible and the partition coefficient P of the substance between the first and second liquid is greater than 1.

2. The method according to claim 1, wherein the porous particle comprises a plurality of pores each having a pore surface.

3. The method according to claim 2, wherein said pore surface has a higher affinity for the first liquid than for the second liquid.

4. The method according to claim 1, wherein said superparamagnetic material is coated with an inert synthetic polymer.

5. The method according to claim 1, wherein the superparamagnetic material is ferric oxide.

6. The method according to claim 1, wherein the porous particle comprises a natural or a synthetic hydrophilic polymer.

7. The method according to claim 6, wherein said hydrophilic polymer is selected from the group consisting of agarose, dextran, cellulose, polyvinyl alcohol, polyacrylamide, hydrophilized polymers and silica glass.

8. The method according to claim 1, wherein the porous particle comprises a natural or a synthetic hydrophobic polymer.

9. The method according to claim 8, wherein said hydrophobic polymer is selected from the group consisting of polyvinyl benzene, polymethacrylate, polystyrene, polypropene and polythene.

10. The method according to claim 8, wherein the first liquid is hydrophobic and the second liquid is hydrophilic.

11. The method according to claim 1, wherein the porous particle comprises a surface coated or coupled or functionalized with a hydrophobic agent.

12. The method according to claim 11, wherein said hydrophobic agent is selected from the group consisting of a hydrocarbon group, an aliphatic group and an aromatic group.

13. The method according to claim 1, wherein the porous particle comprises a surface coated or coupled or functionalized with a hydrophilic agent.

14. The method according to claim 13, wherein said hydrophilic agent is selected from the group consisting of a polysaccharide, agarose, dextran, cellulose, sugar, sorbitol and manitol.

15. The method according to claim 1, wherein the first liquid is hydrophilic and the second liquid is hydrophobic.

16. The method according to claim 1, wherein the mean particle diameter of the porous particle is in the range of 5 µm to 1000 µm.

17. The method according to claim 1, wherein the mean particle diameter of the porous particle is in the range of 30 µm to 200 µm.

18. The method according to claim 1, wherein the volume of the second liquid is selected from the group in the range of 1 µl to 10 µl, 10 µl to 100 µl, 100 µl to 1 ml, 1 ml to 1 L and 1 L to 10 L.

19. The method according to claim 1, wherein the method of separating the porous particle from said second liquid is by magnetic separation.

20. The method according to claim 1, wherein the method of separating the porous particle from said second liquid is by centrifugation.

21. The method according to claim 1, wherein the method of separating the porous particle from said second liquid by filtration.

22. The method according to claim 1, wherein the method is for use in separating, purifying or concentrating a substance which is present alone or in a mixture in a liquid.

23. The method according to claim 1, wherein the substance is a synthetic compound.

24. The method according to claim 1, wherein the substance is an organic molecule and/or biological molecule.

25. The method according to claim 1, wherein the substance is selected from the group consisting of lipid, nucleic acid, protein, glycoprotein, glycopeptide, phosphoprotein, phosphopeptide and carbohydrate.

26. The method according to claim 1 wherein the substance is selected from the group consisting of agrochemical, pesticide, plasticizer, drug, cosmetic, dye and environmental pollutant.

* * * * *